United States Patent [19]
Senitzky

[11] 3,986,769
[45] Oct. 19, 1976

[54] VAPOR DENSITY DEPENDENT OPTICAL FILTER

[75] Inventor: Benjamin Senitzky, Plainview, N.Y.

[73] Assignee: Research Corporation, New York, N.Y.

[22] Filed: Dec. 6, 1974

[21] Appl. No.: 530,223

[52] U.S. Cl. .................................. 350/312; 356/87; 356/187
[51] Int. Cl.² .................... G02B 5/24; G01J 3/30
[58] Field of Search ............... 350/312, 311, 316, 3, 350/168, 172, 173, 147, 160 R, 163; 356/87, 187, 114, 118, 75; 250/574

[56] References Cited
UNITED STATES PATENTS

| | | | |
|---|---|---|---|
| 3,516,744 | 6/1970 | Hinman et al. | 356/75 |
| 3,610,757 | 10/1971 | Valkenburg et al. | 356/75 |
| 3,623,797 | 11/1971 | Daw | 350/312 |
| 3,708,218 | 2/1973 | Smillie | 350/3 |

Primary Examiner—John K. Corbin
Assistant Examiner—Jon W. Henry
Attorney, Agent, or Firm—Cooper, Dunham, Clark, Griffin & Moran

[57] ABSTRACT

A device for filtering a selected spectral line from an incident beam of radiation in the form of a cell which contains an atomic vapor of a material, one of whose spectral lines is the selected spectral line, and which has a window which is non-reflective of incident radiation in the region of the selected spectral line when the vapor is absent. The density of the vapor in the cell may be adjusted to an optimum value at which the window-vapor interface will specularly reflect the selected specular line while passing all other wavelengths in the incident beam into the cell.

21 Claims, 9 Drawing Figures

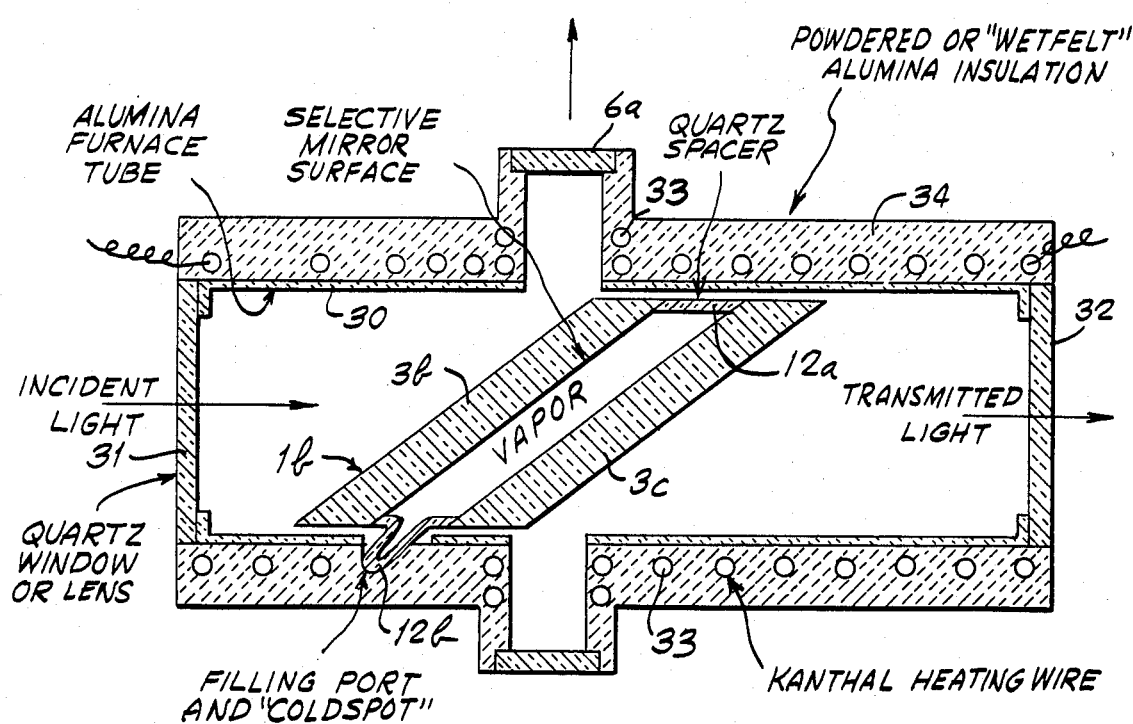
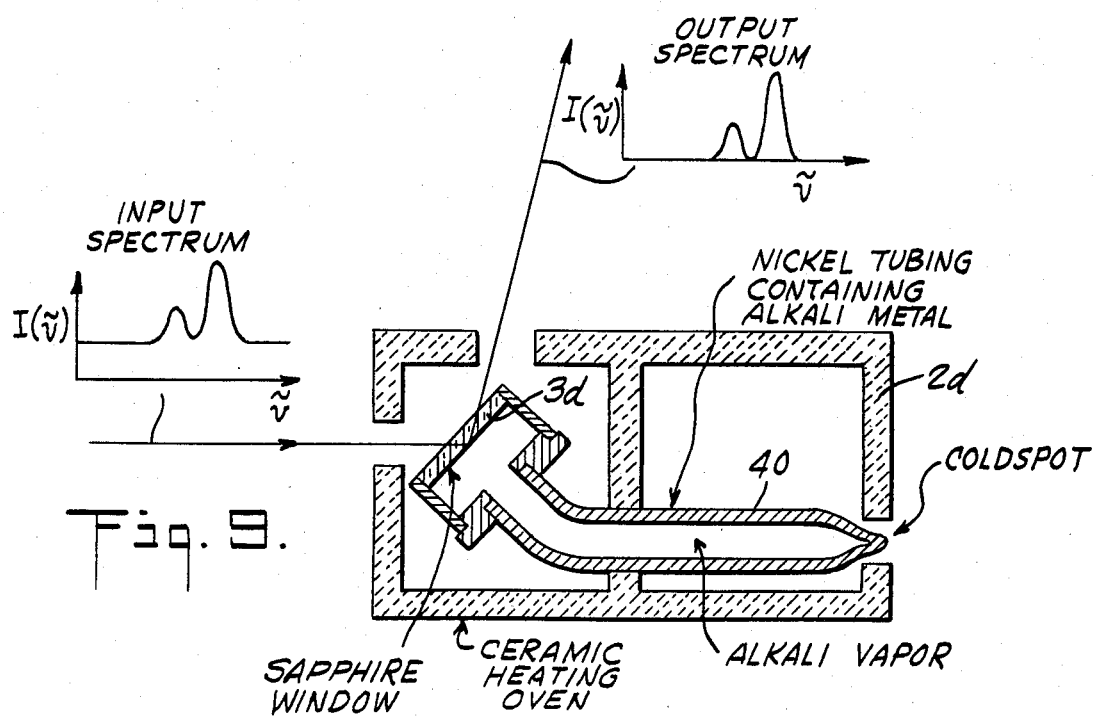

VAPOR DENSITY DEPENDENT OPTICAL FILTER

REFERENCE

The invention herein described was made in the course of or under a contract or subcontract thereunder, with the Department of the Air Force.

BACKGROUND OF THE INVENTION

The present invention involves a spectral line filtering device and more particularly an optical filter utilizing atomic vapor and the phenomenon of selective specular reflection.

Currently in the optical art there is a need for narrowband filters which can be selectively matched to particular spectral lines since atomic spectral line widths are of the order of 0.01–0.1 Angstroms while commonly available filters, such as interference filters or monochromators, range from 1 to 100 Angstroms in bandwidth.

It has long been known that an atomic vapor will absorb and reradiate incident radiation of a resonant wavelength, but the application of the phenomenon for filtering purposes has only recently been appreciated and utilized in the "volume effect" mode in a filter device disclosed in U.S. Pat. No. 3,504,216. More particularly, such reradiated energy consists of two reflection components. One component is roughly at the same wavelength as the incident energy absorbed and is scattered in all directions so that the vapor functions as a diffuse reflector. This type of reflection is referred to as "volume effect" reflectance since the absorption and reradiation occur within the volume of the vapor. The other reflection component is at the exact wavelength of the absorbed incident energy and arises from interference effects between neighboring atoms. Because the atomic positions in a vapor are random, constructive interference will occur only when the angle of incidence of the energy is equal to the angle of reflection. Given this condition a vapor may function as a specular reflector, that is, in the manner of a mirror, for incident energy of the exact wavelength absorbed. This type of reflectance is referred to as "surface effect" reflectance since the absorption and reradiation occur at the surface region of the vapor.

The relative strengths of the specular and diffuse reflections from any atomic vapor will depend, among other factors, upon the atomic density of the vapor, and the particular spectral line absorbed will depend upon the element vaporized. Specular reflection will predominate in most cases only at pressures of several Torr or greater.

The recently developed prior art vapor filters, such as disclosed in U.S. Pat. No. 3,504,216, have used the "volume effect" mode of atomic vapor reradiation while the "surface effect" mode has generally been ignored and little appreciated. Accordingly, the present invention is intended to provide an optical filter, using the "surface effect," which has a narrow bandwidth in the range of 0.1 Angstrom and yet a comparatively large light acceptance angle and area, and unlike the "volume effect" filters, can be used for both absorption and emission spectrometry.

SUMMARY OF THE INVENTION

The present invention involves an optical filter utilizing the selective specular reflection properties of atomic vapors and more particularly embodies a device wherein an atomic vapor is contained in a cell provided with a window which is non-reflective of radiation in the region of the spectral line to be filtered when the vapor is absent. The density of the vapor in the cell is adjusted to an optimum value, such as by placing the cell within an appropriate oven and heating it to achieve the desired atomic density. An incident beam of radiation containing the spectral line to be filtered and background noise may be appropriately prefiltered, polarized and directed through the window-vapor interface which may be arranged at an appropriate angle to avoid undesirable reflection therefrom. To filter a particular spectral line of an element from the beam, the vapor is composed of atoms of that element which when adjusted to an appropriate vapor density will behave as a metallic mirror at the window-vapor interface for energy in the beam of the selected spectral line wavelength while all the other wavelengths will pass into the cell and not be reflected.

It has been found that such surface effect filters require less power to operate and can function with input signals that are orders of magnitude weaker than those required by volume effect filters. In addition, they produce an output signal which is 4 or 5 orders of magnitude greater than the signals of volume effect filters or monochromators. Further, they may be made smaller in size and require less optics and less sensitive readout phototubes than prior art optical filters.

BRIEF DESCRIPTION OF THE DRAWINGS

FIG. 8 is a detailed diagrammatic representation of a preferred embodiment of vapor filter for use in the "spectrometer" of FIG. 7.

FIG. 9 is a diagrammatic illustration of an embodiment of an alkali vapor filter in accordance with the present invention.

DETAILED DESCRIPTION OF THE PREFERRED EMBODIMENT

Figure 1:
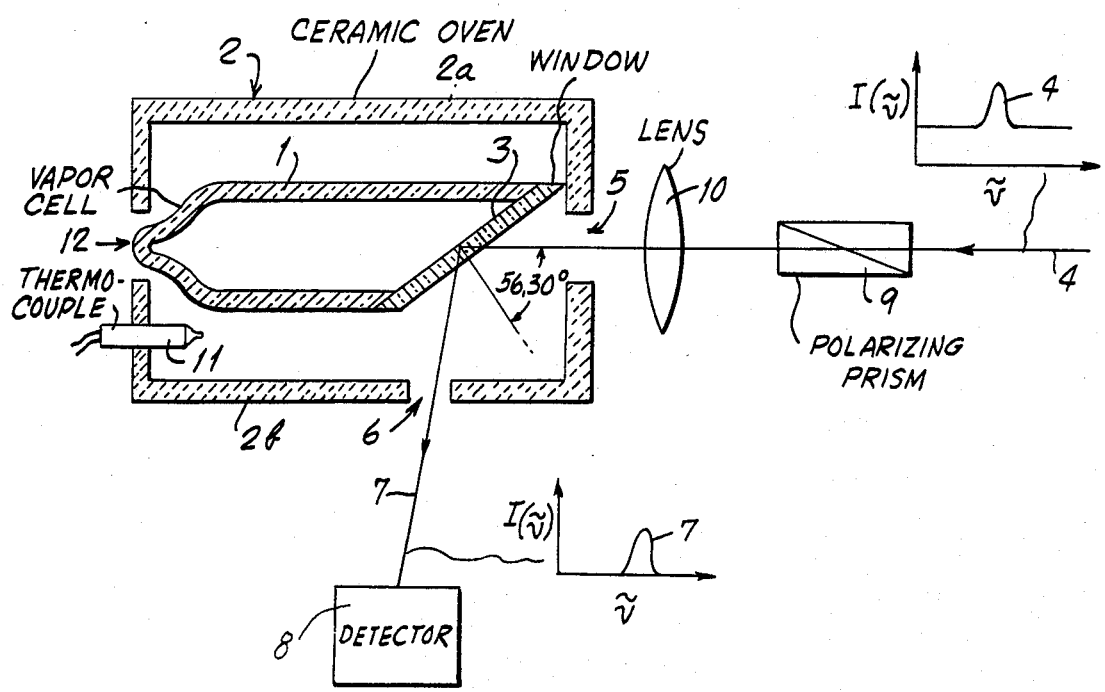
FIG. 1 is a diagrammatic view of a vapor filter in accordance with the present invention.

An optical filter system in accordance with the present invention is shown in FIG. 1 and broadly comprises an hermetically-sealed cell 1 containing an atomic vapor of an element having a spectral or resonance line which is to be filtered from an incident light beam. A means for adjusting the vapor density in the cell may be provided in the form of a cylindrical oven 2 in which the cell 1 is axially disposed and heated to regulate the vapor pressure. The cell 1 has a transparent end window 3 of a suitable material such as quartz arranged to be non-reflective of the line to be filtered from the incident light beam 4, which beam enters the cylindrical oven 2 through an end opening 5. The oven 2 also has a side opening 6 therein to permit the passage of the filtered spectral line 7, after reflection by the vapor, so that it may be detected or used by a suitable utilization device 8. The light beam 4 is suitably transmitted along the long axis of the cell for incidence on the cell window 3.

When the atomic vapor in the cell 1 is of an element such as mercury at a relatively low pressure, that is, less than $10^{-1}$ Torr, and is irradiated with light containing radiation at the resonance wavelength of the vapor element (e.g. 2537 A for mercury vapor), the intensity and spectral width of the reradiated light at 2537 A depends on the temperature, pressure and concentration of foreign gas molecules in the mercury vapor. At the low vapor pressure, the reradiated light will be observed to be incoherent with the exciting radiation and is radiated at all angles.

As the pressure is increased such as by increasing the temperature of the oven, the intensity of the reradiation increases and becomes confined to the surface of the vapor where the incident light enters. Roughly speaking, the vapor behaves as a diffuse reflector. The intensity of the diffusely reflected radiation goes through a maximum at 0.3 Torr and then decreases. At the same time a component of the reradiated light appears in the direction of the specular reflection, which component is unaffected by quenching impurities. At still higher pressures the specular component predominates and the vapor becomes a selective specular mirror for the resonance wavelength, reradiating it through the opening. Thus, at increased pressure and density the vapor will act as a narrow-band optical filter or highly reflective monochromatic mirror.

The basic principles of operation of the system as a suitable optical filter may be more clearly understood in view of the following theoretical considerations which are offered as working hypotheses.

THEORETICAL CONSIDERATIONS

1. Low pressure

Neglecting the effects of hyperfine structure, a vapor of an element such as mercury may be represented by a two-level quantum system where most of the atoms are in the ground state. Also assuming that an incident plane wave with a bandwidth which is broad compared to the atomic linewidth induces transitions between the atomic levels and populates the upper state, and further that the incident radiation is sufficiently weak so that the upper level population is much smaller than that of the ground state, then from a quantum viewpoint, two significant types of radiation processes can be distinguished: (1) a photon is absorbed by a ground state atom which makes a transition to an upper level and at a later time the atom spontaneously emits a photon in the neighborhood of the resonance ground state; and (2) a photon is scattered by the atom, i.e., the incident photon is annihilated and the scattered photon is created at the same time. In the latter case the atom remains in the ground state before and after the collision. When many atoms are involved, coherence effects become important and only two scattering directions are significant. These directions correspond to the refraction and reflection directions of a medium characterized by a macroscopic susceptibility. The susceptibility accounts for scattering and absorption but not for the absorption of a quantum and the subsequent reemission of a quantum at a later time.

The following classical model can be used to describe the above phenomena. The reradiated field can be considered as originating on an aggregate of dipoles (or atomic currents) each of whose moment is the sum of an induced component, coherent with the applied field, and a random component with a spectral power density in the neighborhood of the atomic resonance frequency. In the proposed case both vanish in the absence of the applied field. The radiation from the coherent component accounts for absorption, refraction and specular reflection whereas the random component gives rise to diffuse reflection.

Considering the coherent component first and representing the time variation of an electric field as the real part of $e^{-i\omega t}$, the complex susceptibility for a Doppler and collision-broadened line may be written as:

$$\chi(\omega) = \left(n_1 - \frac{g_1}{g_2}n_2\right) \frac{\tau\sigma_p}{4\pi^2} \int_{-\infty}^{\infty} \frac{e^{-a^2u^2}du}{(\omega_a-\omega)\tau-bu-i} = \chi'(\omega)+i\chi''(\omega) \qquad (1)$$

where $n_1$ and $n_2$ are the population densities of the lower and upper level, $g_1$ and $g_2$ are the degeneracies of these levels, $\tau$ is the phase relaxation time due to collisions, $\omega$ is the frequency of the applied field, $\omega_a$ is the atomic resonance frequency and $u$ is the atomic velocity. Furthermore, $a = (m/2kT)^{1/2}, b = \omega_a\tau/c$ and $\sigma_p = a\lambda_a^3(g_2/g_1) A'_{21}/(8\pi^{3/2})$, where $m$ is the atomic mass, $k$ is Boltzmann's constant, $T$ is the absolute temperature of the vapor, $c$ is the velocity of light in vacuum, $\lambda_a$ is the resonant wavelength and $A'_{21}$ is the Einstein A coefficient for the free atom which is related to the line strength.

An incident wave with a spectral power density $P_i(\omega)$ will give rise to a specularly reflected wave with a spectral power density, $$P_s(\omega) = |\Gamma(\omega)|^2 P_i(\omega), \qquad (2)$$

where $\Gamma(\omega)$ is the reflection coefficient which can be computed from (1) using the Fresnel equations and $|\Gamma(\omega)|^2$ is the reflectance. If the incident power spectrum is broad compared to the reflectance bandwidth, then $$P_s(\omega) = |\Gamma(\omega)|^2 P_i(\omega_a). \qquad (3)$$

The reflectance is a function of the angle the incident wave makes with the surface normal and the polarization of the electric field of the incident wave.

Considering mercury vapor pressures in the range of one Torr or less, where $\chi(\omega)$ is much smaller than unity, the reflectance for Brewster's angle incidence will vary as $|\chi(\omega)|^2$ whereas for normal incidence it will vary as $(1-8\pi\chi'(\omega))$. Since $\chi(\omega)$ increases with pressure, $|\Gamma(\omega)|^2$ also increases with pressure. It can further be shown that the specular reflectance continues to increase as the pressure is increased above 1 Torr.

To now estimate the reradiation due to the incoherent component of the dipole moment which gives rise to diffuse reflectance, the excited population, $n_2$, may be computed from a rate equation. Further assuming that in the proposed case the spontaneous emission radiation is the same whether the atom is excited by a broadband plane wave or by thermal radiation, since at the pressures of interest nonthermal polarization effects are insignificant, it will be found that the power emitted per unit volume per unit frequency interval, $P_d(\omega)$, is $$P_d(\omega) = 4\pi(A_{21} + \tau_{21}^{-1})^{-1}A_{21}\omega_a\chi''(\omega)\rho_i(\omega_a), \quad (4)$$

where $A_{21}$ is the spontaneous emission at the volume element of interest, $\rho_i(\omega_a)$ is the energy density per unit frequency interval of the incident plane wave and $\tau_{21}^{-1}$ is the collisional decay rate from the upper to the lower level. Although coherent radiation effects have been neglected, this is justified at low pressures since the numbers of atoms per cubic wavelength is small. In this range $A_{21}$ and $A'_{21}$ are equal. At high pressures coherent radiation effects can still be neglected since the collisions tend to destroy the phase correlations of adjacent atoms. But $A_{21}$ and $A'_{21}$ will differ because the radiating atoms will be affected by their electromagnetic environment which consists of the cell window and the dielectric properties of the other atoms. A technique for evaluating $A_{21}/A'_{21}$ can be adapted to the problem. The radiation represented by (4) will be emitted at all angles and gives rise to a diffuse reflectance.

The sum of the specular reflectance term (3) and the diffuse reflectance term (4) can qualitatively explain the initially described phenomena. Accordingly, when the medium is optically thin the diffusely reradiated power spectrum will be proportional to (4). As the pressure is increased the diffuse reflectance will at first increase due to the increase in $\chi''(\omega)$. As the medium becomes opaque the volume contribution to the reradiation decreases and the diffuse reflectance decreases in agreement with observation. The diffuse reflectance depends on non-radiative quenching through the factor $\tau_{21}^{-1}$ in (4), but the specular reflectance is unaffected by this term. This fact is also in agreement with observation. The specular reflectance term in (3) continues to increase with pressure, therefore it should be expected to become the dominant term at higher pressures as observed.

Now the higher pressure range will be considered in a more quantitative manner and then the theoretical predictions will be compared with actual measurements.

2. High Pressure

As the vapor pressure is increased above one Torr into the atmosphere pressure range, the collision broadening masks the hyperfine structure and the assumption of a two level quantum system becomes valid for natural mercury. Equation (1) simplifies to $$\chi(\omega) = \frac{\chi_o''}{(\omega_a-\omega)\tau-i}, \quad (5)$$

where $$\chi''_o = n_1\tau\lambda_a^3(g_2/g_1)A'_{21}/(32\pi^3). \quad (6)$$

Since the susceptibility is not small compared to one, the local and macroscopic field differ and the above equation becomes $$\chi(\omega) = \frac{\chi_o''}{(\omega_a+\Delta\omega-\omega)\tau-i}, \quad (7)$$

where $$\Delta\omega = -\frac{4\pi n_1}{3} \frac{g_2}{g_1} \frac{A_{21}'}{32\pi^3}\lambda_a^3. \quad (8)$$

Equation (7) will be found to agree with observation if the quantities $\chi''_o$, $\Delta\omega$ and $\tau$ in the above equations are properly chosen. For the applications to be described below, the optimum mercury vapor pressure is two atmospheres (390°C). At this pressure the measured values are $\chi''_o = 0.109$, $\Delta\omega = 7.5 \times 10^{10}$ sec.$^{-1}$ and $\tau^{-i} = 9.8 \times 10^{10}$ sec.$^{-1}$. The susceptibility at line center, $\chi''_o$, corresponds to a photon absorption cross-section of $\sigma_p = 5 \times 10^{-13}$ cm$^2$, which will be found in agreement with low pressure absorption measurements. The relaxation rate $\tau^{-1}$, is about 3.7 times smaller than that obtained by extrapolating the low pressure values under the assumption that $\tau^{-1}$ is proportional to pressure and the measured frequency shift, $\Delta\omega$ is roughly twice the value computed from (8).

The dielectric constant for mercury vapor at two atmospheres pressure can therefore be written as $$\epsilon(\omega) = 1 + \frac{4\pi\chi_o''}{(\omega_a+\Delta\omega-\omega)\tau-i}, \quad \begin{array}{l}\chi_o''=0.109\\ \Delta\omega=-7.5\times10^{10}\text{sec}^{-1}\\ \tau^{-i}=9.8\times10^{10}\text{sec}^{-1}\end{array} \quad (9)$$

from which vapor filter reflectance characteristics may be computed in the following manner.

3. Reflectance

Figure 2:
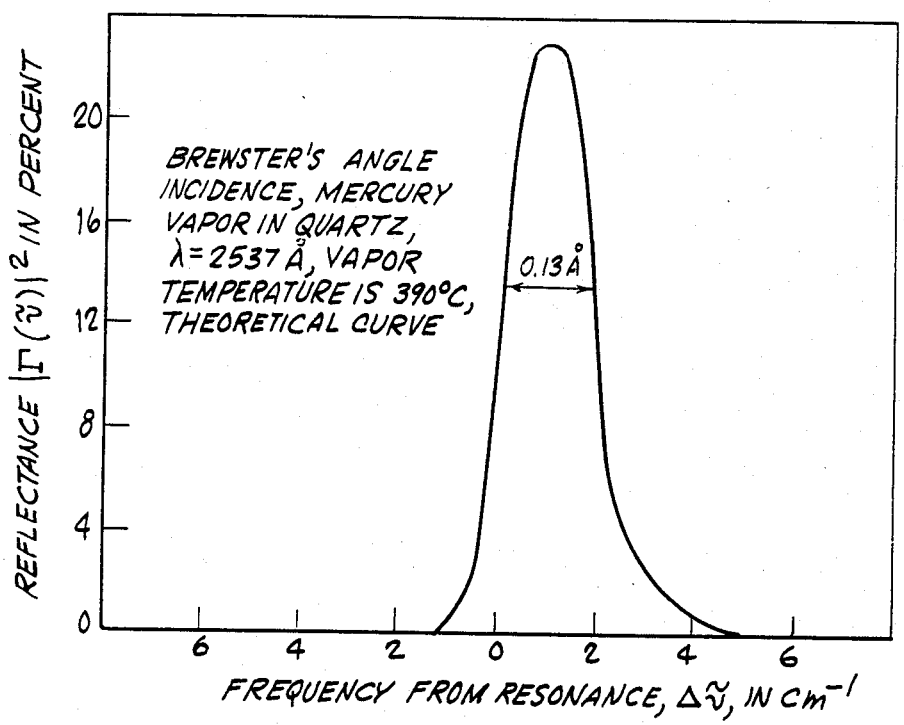
FIG. 2 is a plot of the theoretically computed spectral response of a mercury vapor filter showing the reflectance in percent versus the frequency deviation from resonance in $cm^{-1}$.

In the atmosphere pressure range the mercury vapor can be regarded as a medium with a magnetic permeability of one and a frequency dependent dielectric constant $\epsilon(\omega)$. It may be contained in quartz with a frequency independent real dielectric constant $\epsilon_1$. When the propagation direction of the incident plane wave, the normal to the quartz-vapor interface and the electric field are coplanar, the complex reflection coefficient becomes $$\Gamma(\omega) = \frac{\epsilon(\omega)\cos\theta_1 - \sqrt{(\epsilon(\omega)-\epsilon_1\sin^2\theta_1)\epsilon_1}}{\epsilon(\omega)\cos\theta_1 + \sqrt{(\epsilon(\omega)-\epsilon_1\sin^2\theta_1)\epsilon_1}}, \quad (10)$$

where $\theta_1$ is the angle in the quartz between the propagation direction of the plane wave and the normal to the quartz-vapor interface. At Brewster's angle for the quartz-vacuum interface, only the vapor will contribute to the reflectance. Operating at this angle ($\theta_1 = 33.7°$) and at a wavelength of 2537 A, the reflectance at a vapor pressure of two atmospheres can be computed using 10 and is plotted in FIG. 2 as a function of the deviation in wavenumbers from the low pressure natural mercury resonance. The 0.13 A wide filter characteristic has a 23% peak reflectance. The "blue shift" towards shorter wavelengths occurs because below resonance the real part of the vapor dielectric constant becomes larger than unity and tends to match the quartz dielectric constant whereas above resonance the opposite effect occurs and there is a greater mismatch and reflection. This effect predominates over the "red shift" $\Delta\omega$, which increases with increasing mercury vapor pressure. A further "red shift" can be achieved by using isotope $Hg^{204}$ or by adding an inert gas such as argon (the low mercury-argon collision crosssection implies that the characteristic in FIG. 2 will not be appreciably broadened).

4. Noise

A source of noise in the vapor filter is the thermal background at the detector in the absence of incident energy. Since this energy is concentrated mainly in the far infrared, it can be readily rejected at the detector. Further background rejection can be achieved by properly arranging the optics so that the output detector sees an open port.

Diffuse vapor reflectance in the device can arise not only from the individual incoherent dipole moment of atoms as described above, but from turbulence in the vapor and from optical inhomogeneities in the quartz windows. This radiation contributes to the signal when the output is spatially integrated as in spectrochemical analysis and contributes to the noise if the filter is used in such an application as monochromatic photography. Diffuse reflectance noise will be found to be insignificant in the monochromatic photography application to be described below.

Empirical Considerations and Observations

Using an optical filter system such as shown schematically in FIG. 1 it has been observed that the resulting phenomena, as measured, conform closely to the theoretical predictions as given above. Thus, drawing on the theoretical analysis, the basic requirements for constructing and operating a preferred optical filter system will be more fully appreciated. For example, since the reflection being utilized occurs from the surface of the vapor at the window-vapor interface, it is extremely important, in constructing a system in accordance with the invention, that the cell window be non-reflective of spectral lines in the immediate vicinity of the spectral line to be filtered; that is, the window, at its outer interface with the ambient atmosphere of the cell and at its inner interface with the interior of the cell in the absence of the vapor, should be non-reflective of radiation in a bandwidth of about 1 A or greater containing the spectral line of interest. This non-reflectivity may be accomplished in various ways, such as, for example, by the application of a suitable antireflection coating to the inner and outer window surfaces. The coating must be selected to be of a material having a refractivity which in combination with the refractivity of the window material will pass radiation in a bandwidth of about 1 A or greater containing the spectral line to be filtered. An alternate means for accomplishing this range of non-reflectivity and that which is presently preferred, is to arrange the window member with respect to the incident beam of radiation at Brewster's angle for the spectral line to be filtered and to polarize the radiation beam for Brewster's angle incidence on the window. Such an arrangement will achieve the non-reflection of radiation in the immediate vicinity of the spectral line to be filtered, and radiation beyond that vicinity may be prefiltered or may be removed after reflection by the detector or utilization device.

Turning now to the construction and operation of a preferred optical filter system, such as shown schematically in FIG. 1, it will be seen that the basic components comprise: a cell 1 for containing the vapor of a material, one of whose spectral or resonance lines is the spectral line to be filtered from an incident beam 4 of radiation; a window 3 in the cell through which the radiation beam 4 passes into the cell; and a means for adjusting or regulating the density of the vapor in the cell to produce specular reflection of the spectral line of interest from the beam of radiation, which means in FIG. 1 is a cylindrical oven 2 for heating the vapor. Although atomic vapors are most suitable, and the preferred embodiment will be described in connection therewith, it is contemplated that molecular vapors, having resonance lines in the microwave or millimeter range due to rotational frequency, may also be found suitable.

In the particular embodiment shown in FIG. 1 the vapor is selected to be of mercury and the cell and its window is of quartz. Liquid mercury may be distilled into the quartz cell and the cell 1 then placed between the ceramic heating elements 2a, 2b which constitute the two halves of the cylindrical oven 2, whose dimensions in practice are of the order of 2½ inches in diameter and 4 inches in length. The window 3 in the cell is arranged at Brewster's angle with respect to the incident beam of radiation 4 for the spectral line to be filtered, which is the case of mercury will be 2537 A. The radiation beam 4 is polarized at 9 and collimated by a suitable lens 10 and transmitted along the long axis of the cell 1 for Brewster's angle incidence on the window 3, that is, at 56.3° to the quartz-air interface.

The cell 1 is heated in the oven 2 to increase the vapor pressure of the mercury in the cell to a point where the vapor density will produce specular reflection of the 2537 A line. A thermocouple 11 may be used to read the oven temperature and a "cold spot" 12 may be provided in the cell at a lower temperature than that within the oven 2 for trapping the vapor to localize vapor condensation. The specularly reflected light spectrum 7 may be analyzed with a suitable utilization or detector device 8 which may be, for example, a spectrometer adjusted to resolve 0.2 wave numbers for checking the filter characteristics.

With the above-described system it will be found that a residual wideband reflectance of 0.02% is measured at an acceptance angle of 7° when the vapor is at room temperature. The resultant residual reflectance is due to (a) the perpendicular polarization component transmitted by the polarizer, (b) the depolarizing effect of strains in the quartz window, and (c) deviations from the exact Brewster's angle. As the vapor temperature increases, the skirt reflectance will remain at 0.02% but the reflectance at resonance (2537 A) increases to roughly 14% yielding a signal-to-skirt rejection ratio of 700.

More particularly, since the filter system must reject radiation over wavelength ranges which are three orders of magnitude greater than its passband, its skirt rejection becomes an important parameter. In an actual application, the pertinent skirt rejection ratio is the ratio between the reflectance at the wavelength to be filtered and the reflectance at the skirts. It will be observed that the reflectance of the heated cell far from resonance, i.e., at the skirts, is equal to the reflectance of the cold cell at resonance. The skirt rejection ratio may therefore be measured using a mercury line source (Pen-Ray) for the radiation beam in FIG. 1 and a photodetector and recorder for the utilization of detector device 8. The ratio between the reflected signals with the hot and cold cell is the skirt rejection ratio. Absolute reflectance is determined by calibrating against the known reflectance at the quartz-vacuum interface when the radiation is polarized for maximum reflectance (14.4%).

Figure 3:
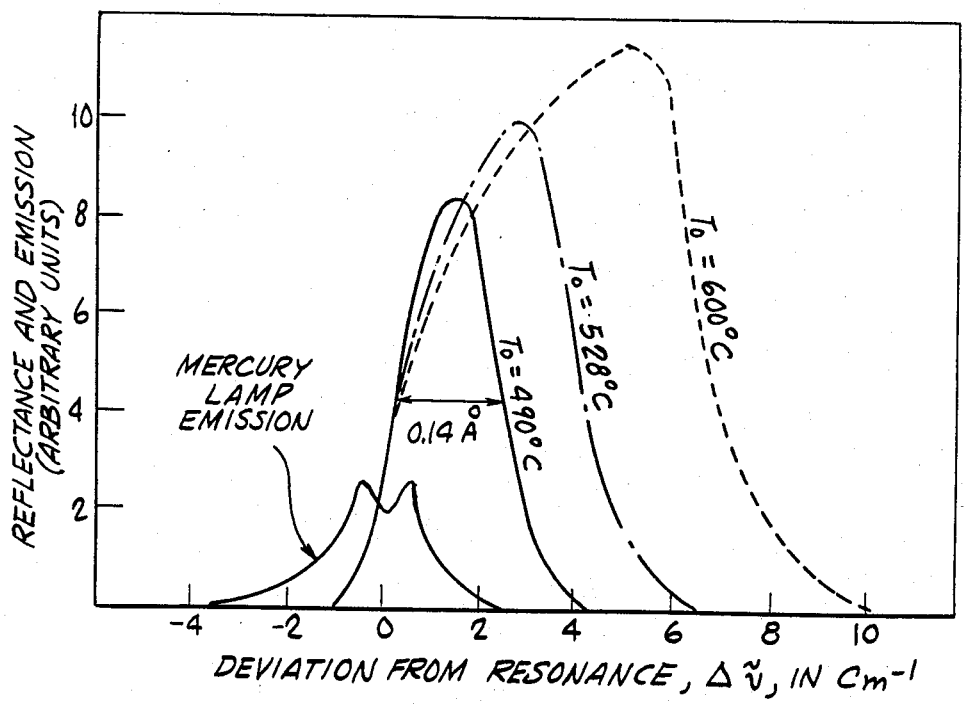
FIG. 3 is a plot of the observed reflectance of a mercury vapor filter versus deviation from resonance at different oven temperatures.

The measured specular reflectance characteristics of the mercury cell are shown in FIG. 3 for various oven temperatures. The structure and width of the mercury lamp are due to self-reversal. A 490° C oven temperature, or about 390° C vapor temperature, may be attained with 20W of line power and corresponds to an estimated vapor pressure of about two atmospheres. It will be seen that the measured 0.14 A bandwidth curve is in agreement with the computed curve shown in FIG. 2. This oven temperature is believed to be optimum for the application to be described below. The maximum reflectance shown in FIG. 3 is about 40%. This value is greater than that which may be achieved with most metals at this wavelength.

Figure 4:
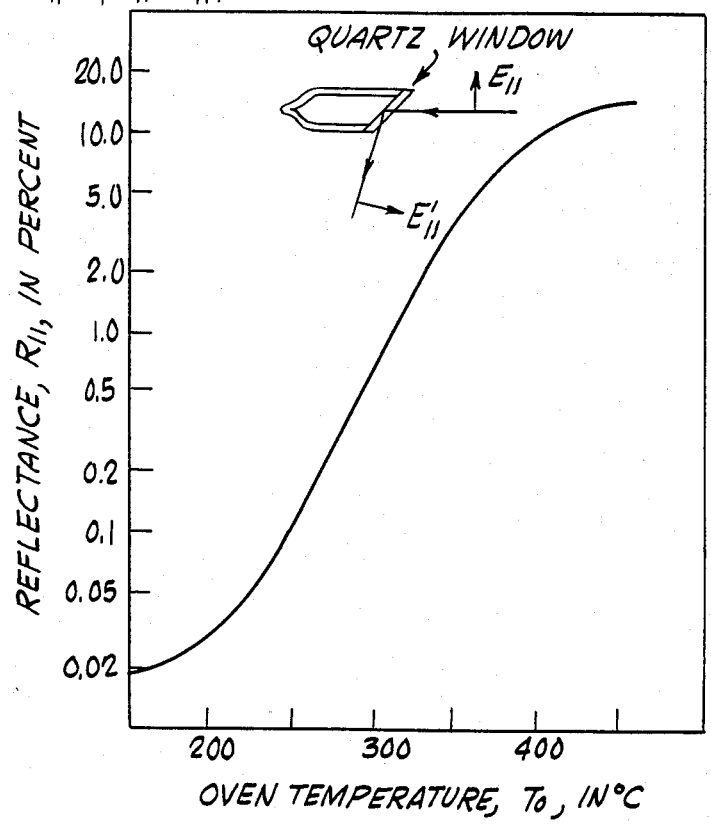
FIG. 4 is a plot of the reflectance in the vicinity of resonance as a function of temperature.

A plot of the reflectance of the signal as a function of temperature is shown in FIG. 4. To obtain good skirt rejection, the cell windows must be strain-free to avoid depolarizing effects. As expected from FIG. 3, the reflectance in the vicinity of resonance increases rapidly at first with increasing temperature and then saturates at temperatures above 460°C. The maximum reflectance of 14% can be used to estimate the vertical scale in the measured spectral characteristics in FIG. 3. Again, reference to that figure indicates that the measured absolute reflectance agrees with the theoretical value given in FIG. 2.

The skirt rejection ratio computed from FIG. 4 is 28dB. It may be further increased by somewhat increasing the diameter of the cell and limiting the aperture to the region of the window which is further removed from the fused seals. This will decrease the effects of strain in the quartz window.

The basic optical filter system of the present invention may be utilized in various applications as mentioned above such as in an atomic emission flame photometer or in monochromatic photography.

Figure 5:
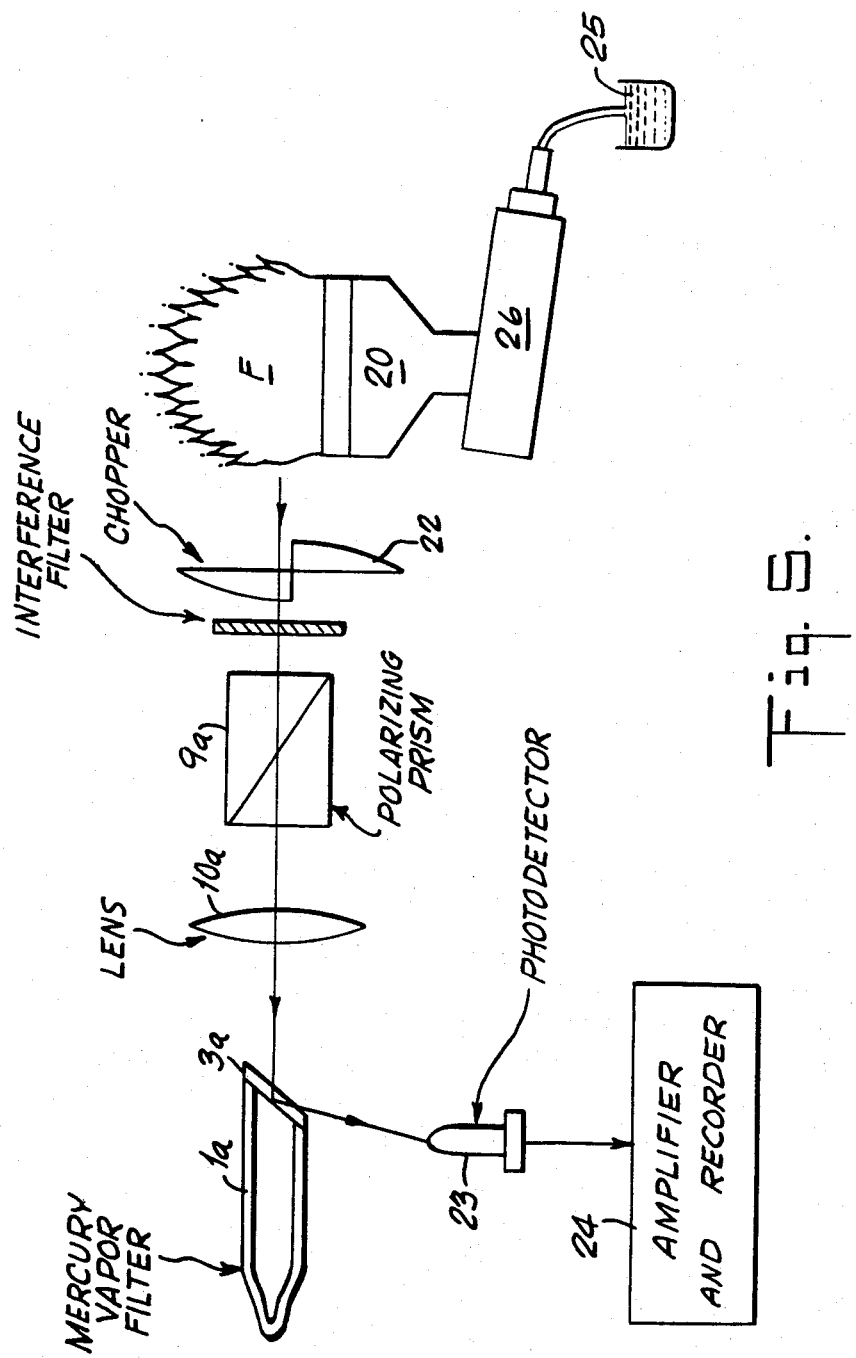
FIG. 5 is a schematic view of a vapor filter in accordance with the present invention incorporated in a flame photometer system.

Firstly, the filter system may be incorporated into an atomic emission flame photometer as shown in FIG. 5 wherein the flame F to be analyzed is produced in a nitrous oxide-acetylene burner 20 with a 0.020 × 2 inch slot. The longer dimension of the burner 20 is arranged parallel to the optic axis of the focussing lens 10a which focusses the radiation on the Brewster's angle window 3a of the cell 1a. A 100 A wide multilayer prefilter and a chopper 22 are disposed between the flame F and the polarizing prism 9a and a photodetector 23 in combination with an amplifier and recorder 24 are used as the utilization device. A blank water solution is first aspirated into the flame from the reservoir 25 by the atomizer 26 to determine the flame background. A solution containing the element to be detected is then aspirated into the flame and appropriate measurements are taken.

Figure 6:
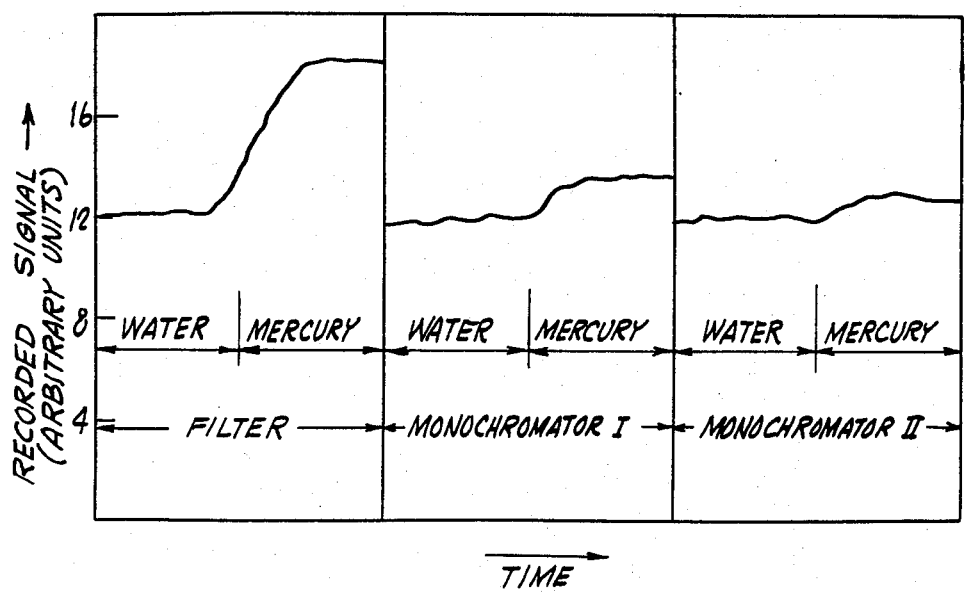
FIG. 6 is a plot illustrating the observed signal-to-background ratio of the output of a flame photometer in accordance with that shown in FIG. 5 as compared with the respective outputs of a 1-Angstrom resolution monochromator and a 2-Angstrom resolution monochromator.

By way of comparison, three detection systems were used to measure a 0.1% mercury solution in water, that is (1) the vapor filter; (2) a monochromator I with a one-Angstrom resolution; and (3) a monochromator II with a two-Angstrom resolution. The results of these measurements are shown in FIG. 6 where it will be seen that the vapor filter yielded the largest signal-to-background ratio.

Figure 7:
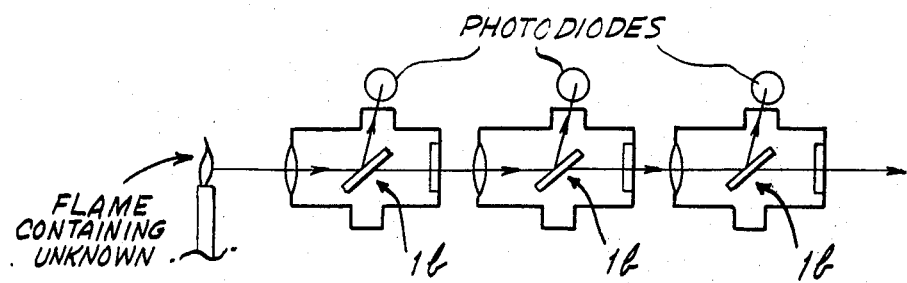
FIG. 7 is a diagrammatic representation of a number of vapor filters in accordance with the present invention arranged in tandem to form a "vapor filter spectrometer."

For applications where the chemical constitution of the sample is entirely unknown, a wavelengths scanning spectrometer would ordinarily be required. However, for the majority of applications the user is interested in the concentration of a limited number of known elements. For example, drinking water may be analyzed for mercury, cadmium, arsenic and lead; blood serum may be analyzed for the alkali metals, calcium, magnesium and iron; and plating plant effluents may be tested for cadmium or chromium. In the many applications in such diverse fields as metallurgy, medicine, agriculture, oceanography and astronomy it is possible to use a series of the present optical filters more conveniently and economically than a conventional grating spectrometer. For example, in a metallurgical application a conventional emission spectrometer has roughly a one-Angstrom resolution with an acceptance angle of 2° and a 0.05 mm wide, 1.3 mm long entrance slit. An array of optical filters in accordance with the present invention, as shown in FIG. 7, can be used to make up a vapor filter spectrometer which will have a 0.14 Angstrom rersolution, a 7° acceptance angle, and a 1 cm$^2$ acceptance area. In this application each of the filter elements 1b in the array is provided also with a Brewster's angle rear or exit window and axially aligned with the other elements. A suitable element of this type is shown in detail in FIG. 8 and comprises a cell 1b with front and rear Brewster's angle windows 3b, 3c, a quartz spacer 12a, and a filling port and "cold spot" 12b, contained in an alumina furnace tube 30 having quartz windows or lenses 31 and 32 for respectively passing the incident and transmitted light. The furnace tube 30 is surrounded by powdered or "wetfelt" alumina insulation 34 through which suitable heating wires 33 are run. The filtered output light passes through the exit window 6a. Each of these filter elements will specularly reflect the characteristic resonance wavelength of its atomic vapor and pass the other wavelengths. Thus, in analyzing drinking water, cells containing mercury vapor, cadmium vapor, arsenic vapor and lead vapor may be serially aligned and their characteristic lines detected simultaneously. This overall "optical filter spectrometer" can be made smaller, more durable and less expensively than conventional grating spectrometers.

It may nevertheless appear that if specific elements are to be detected, the scanning monochromator would be clearly superior to the optical filter system since such a monochromator can compare the measured atomic line intensity to the broad spectral background in the neighborhood of the line. However, it should be considered that in most spectral chemical analyses using either emission or absorption techniques, the intensity of a particular atomic line in an unknown sample is compared with its strength in a reference sample. The broad spectral background is usually a characteristic of the chemical composition of the gases in the flame and the sample host and is not affected by the "impurities" in the sample host. There are a limited number of cases where a particular impurity other than the one under investigation may affect both the background and the line signal. These interferences can occur in all forms of spectral chemical analyses and require the proper corrections. Nevertheless, most analyses can be performed at fixed wavelengths without scanning. It should also be noted that the majority of instruments sold for this purpose, mainly the atomic flame absorption spectrometers, use fixed line sources and do not scan in wavelength, so that the present optical filter systems will be found quite suitable in this application.

A further application of the present vapor filter is as an alternative to a spatially scanning monochromator in analyzing the spatial distribution of a spectral line source using monochromatic photography. This application may be readily accomplished by modifying the arrangement of the apparatus in FIG. 5 to delete the chopper 22 and move the lens 10a into its place and by positioning a camera for photographing the filter output in the place of the utilization device 23, 24. A photograph of the atomic distributions in the flame emitting the resonance wavelength, even at ultraviolet wavelengths, may be obtained with this apparatus. This type of photography can be utilized for flame diagnostics by, for example, seeding the flame with a particular element such as calcium or sodium to determine the temperature profile. Spatial masking may also be used when the spatial distribution of the resonance wavelength differs from the distribution of the flame background to thus enhance the signal-to-background ratio.

Other contemplated applications for the present vapor filters are (1) as replacements for the presently used wideband multilayer filters in fluorescence spectrometers to enhance their sensitivity by a factor of 30; (2) in combination with a deterium or high pressure arc continuum source as a substitute for atomic absorption spectrometers which use hollow cathode or electrodeless spectral line sources and a monochromator; and (3) as a narrowband receiver in optical communications systems.

Further modifications can be made to the basic filter construction to improve the performance. For example, an angle may be introduced between the front and rear surfaces of the front window of the filter cell so that the residual reflectance from the front surface can be rejected. Also, as previously indicated, antireflection coatings may be used to advantage, and multiple reflections from vapor surfaces may be utilized, in a manner equivalent to cascading identical filters, to produce an increased skirt rejection ratio. It is also contemplated that different types of heating arrangements may be used such as mounting the heating elements in a vacuum enclosure in the manner of a vacuum tube or including the heating elements in the window itself and thus eliminating the external oven.

Particularly suitable window materials have been found to be quartz, optical periclase and sapphire. In addition to mercury, which has been found particularly suitable, a number of other elements can be used in the vapor filters as desired, such as listed in the following table:

Table I

| Element | Vapors for Vapor Filters | | |
|---|---|---|---|
| | Wavelength Angstroms | Temperature Range, °C | Vaporization |
| helium | 584 | | thermal |
| neon | 753 | | |
| argon | 1048 | | |
| krypton | 1235 | | |
| xenon | 1469 | | |
| mercury | 1849, 2537 | 200–1000 | thermal |
| zinc | 2139 | | |
| cadmium | 2288 | | |
| lead | 2833 | | |
| indium | 3039 | | |
| strontium | 4607 | | |
| calcium | 4227 | | |
| barium | 5536 | | |
| lithium | 6708 | | |
| sodium | 5890 | | |
| potassium | 7665 | | |

Table I-continued

| Element | Vapors for Vapor Filters | | |
|---|---|---|---|
| | Wavelength Angstroms | Temperature Range, °C | Vaporization |
| rubidium | 7800 | | |
| caesium | 8521 | | |
| iron | 2483 | 1000–1500 | thermal |
| manganese | 2795 | | |
| tin | 2853 | | |
| copper | 3248 | | |
| selenium | 1960 | | discharge |
| arsenic | 1972 | | |
| antimony | 2068 | | |
| tellurium | 2142 | | |

Almost all of these transitions have a greater A coefficient than the mercury 2537 A line, therefore their reflectance can be larger and their bandwidth narrower than that of mercury. Certain modifications must be made to the cell structure such as, in the case of xenon and krypton, several millimeter thick lithium fluoride windows would be in order while the windows for the other noble gases will require special design. Some of the other elements may require cell materials such as boron nitride ovens and sapphire windows. Polyatomic vapors such as arsenic might operate with compact microwave discharge systems where the vapor mirror terminates the coaxial load of a planar triode oscillator. A particular embodiment for an alkali vapor is shown in FIG. 9. The vapor of an alkali metal (Li, Na, K, Rb, Cs) is contained in a nickel tube 40, disposed in a divided ceramic heating oven 2d, with a cell on one end having a sapphire window 3d. The incoming spectrum is shown as constituting the two lines of an alkali doublet which for sodium are about 6 A apart. The filter will reflect both and pass other wavelengths so that in such a case it is "matched" to the fine structure of the line.

In evaluating a particular element the specular reflectance characteristics of its vapor can be computed if the phase relaxation time $\tau$ and the local field frequency shift $\Delta\omega$ are known over the pressure range of interest. The extrapolation of these values from low pressure is based on the assumption that the atoms behave as isolated quantum systems subjected to an isotropic and homogeneous external field except when they interact with other atoms through short duration binary collisions. However, at the higher pressures of interest, these assumptions will not be valid. For example, the estimated "skin depth" of the 2537 A line of mercury is about 520 A at the wavelength of maximum absorption. As a result experimental observation and existing theory do not always agree. At present the susceptibility has been determined from reflectance measurements $|\Gamma(\omega)|^2$. A more direct measurement of $\Gamma(\omega)$ is recommended if narrow sources are used by making the vapor surface one mirror of an interferometer. Further analysis in this area will reduce the experimental and theoretical discrepancy and permit more accurate predictions for the various elements.

I claim:
1. A device for filtering a selected spectral line from an incident beam of radiation comprising:
   a. a vapor of a material, one of whose spectral lines is the selected spectral line to be filtered from the incident beam;
   b. cell means for containing said vapor;
   c. window means in said cell means for passing said beam into said cell means;

d. means for rendering said window means, in the absence of said vapor in said cell means, non-reflective of radiation in at least a bandwidth of approximately 1 A containing said selected spectral line; and e. means for regulating the density of the vapor in said cell means such that said vapor, in combination with said window means, produces specular reflection of said selected spectral line.

2. A device as in claim 1 wherein said means for regulating the vapor density comprises means for heating said cell means.

3. A device as in claim 1 wherein said means for regulating the vapor density comprises means for regulating the vapor pressure.

4. A device as in claim 1 wherein said window means comprises a member having a front surface and a rear surface which is in contact with said vapor, and said non-reflective rendering means comprises an antireflection coating disposed on at least one of said surfaces.

5. A device as in claim 1 wherein said window means comprises a member having a surface forming an interface with the interior of said cell means and said non-reflective rendering means comprises means for arranging said member with said interface at Brewster's angle for said selected spectral line in the incident beam in the absence of said vapor in said cell means and means for polarizing said incident beam for Brewster's angle incidence on said interface.

6. A device as in claim 5 wherein the means for regulating said vapor density comprises a heating oven surrounding said cell means and further comprising means in said oven for passing said spectrally reflected selected spectral line out of said oven.

7. A device as in claim 1 further comprising outlet means in said cell means aligned with said window means for passing the radiation remaining in said incident beam after the spectral reflection of said selected spectral line out of said cell means.

8. A device as in claim 1 further comprising cold spot means in said cell means for trapping said vapor to localize the vapor condensation.

9. A device as in claim 1 wherein said window means is of a material selected from the group consisting of quartz, optical periclase, and sapphire.

10. A method for filtering a selected spectral line from an incident beam of radiation comprising the steps of:

a. introducing a vapor of a material, one of whose spectral lines is the selected spectral line to be filtered from the incident beam, into a chamber;

b. forming a window in said chamber for admitting the incident beam and constructing the window such that, in the absence of said vapor in the chamber, it is non-reflective of spectral lines in at least a bandwidth of approximately 1 A containing said selected spectral line; and c. producing a vapor density in said chamber such that the vapor in combination with said window produces spectral reflection of said selected spectral line.

11. A method as in claim 10 wherein the desired vapor density is produced by heating the chamber.

12. A method as in claim 10 wherein the desired vapor density is produced by regulating the vapor pressure.

13. A method as in claim 10 wherein said window is constructed by the application of an anti-reflection coating to at least line the outer and inner surfaces.

14. A method as in claim 10 wherein said window is constructed by arranging the surface of the window forming an interface with said chamber at Brewster's angle for said selected spectral line in the incident beam in the absence of said vapor in said chamber and comprising the further step of polarizing said incident beam for Brewster's angle incidence of said interface.

15. A method as in claim 10 comprising the further step of providing an outlet in the chamber aligned with said window for permitting the passage of the radiation remaining in said incident beam out of the chamber after the spectral reflection of said selected spectral line.

16. A method as in claim 10 further comprising the step of providing a cold spot in said chamber for trapping said vapor to localize the vapor condensation.

17. A method as in claim 10 wherein said window is of a material selected from the group consisting of quartz, optical periclase, and sapphire.

18. A method as in claim 10 wherein said vapor is of an element selected from the group consisting of mercury, cadmium, lead, calcium, magnesium, and the alkali metals.

19. An optical filter apparatus comprising:

a. an atomic vapor of an element whose resonance line is to be filtered from an incident light beam;

b. cell means for confining said atomic vapor;

c. transparent window means for passing said incident light beam into said cell means and arranged in said cell means with its interior surface at Brewster's angle for said resonance line in said incident light beam in the absence of said atomic vapor in said cell means;

d. means for directing and polarizing said incident light beam for Brewster's angle incidence on said window means; and e. means for producing specular reflection by said atomic vapor of said resonance line to filter said resonance line from said incident light beam.

20. Apparatus as in claim 19 wherein said specular reflection producing means comprises means for producing a vapor pressure of at least one atmosphere in said cell means.

21. Apparatus as in claim 19 wherein said specular reflection producing means comprises means for heating said cell means.

* * * * *

UNITED STATES PATENT OFFICE
CERTIFICATE OF CORRECTION

Patent No. 3,986,769      Dated October 19, 1976

Inventor(s) Benjamin Senitsky

It is certified that error appears in the above-identified patent and that said Letters Patent are hereby corrected as shown below:

Col. 6, equation (9), the denominator should read $(\omega_a + \Delta\omega - \omega)\tau^{-1}$ Col. 14, line 12, "line" should be dlleted and -- one of -- inserted therefor.

Signed and Sealed this

Twenty-sixth Day of April 1977

[SEAL]

Attest:

RUTH C. MASON
*Attesting Officer*

C. MARSHALL DANN
*Commissioner of Patents and Trademarks*